United States Patent
Davidson

(10) Patent No.: US 7,211,248 B2
(45) Date of Patent: May 1, 2007

(54) ENHANCEMENT OF TRANSFECTION OF DNA INTO THE LIVER

(75) Inventor: Michael Davidson, Highland Park, IL (US)

(73) Assignee: SonoGene, L.L.C., Glen Ellyn, IL (US)

(*) Notice: Subject to any disclaimer, the term of this patent is extended or adjusted under 35 U.S.C. 154(b) by 0 days.

(21) Appl. No.: 10/483,189

(22) PCT Filed: Jul. 10, 2002

(86) PCT No.: PCT/US02/21620

§ 371 (c)(1),
(2), (4) Date: Aug. 4, 2004

(87) PCT Pub. No.: WO03/006608

PCT Pub. Date: Jan. 23, 2003

(65) Prior Publication Data

US 2004/0248832 A1 Dec. 9, 2004

Related U.S. Application Data

(60) Provisional application No. 60/303,784, filed on Jul. 10, 2001.

(51) Int. Cl.
*A61K 48/00* (2006.01)
*A01N 63/00* (2006.01)
(52) U.S. Cl. .................................................. 424/93.2
(58) Field of Classification Search ............... 424/93.2
See application file for complete search history.

(56) References Cited

U.S. PATENT DOCUMENTS

| | | | |
|---|---|---|---|
| 5,190,766 A | 3/1993 | Ishihara et al. | |
| 5,498,421 A | 3/1996 | Grinstaff et al. | |
| 5,542,935 A * | 8/1996 | Unger et al. ............... | 604/190 |
| 5,558,092 A | 9/1996 | Unger et al. | |
| 5,580,575 A | 12/1996 | Unger et al. | |
| 5,770,222 A * | 6/1998 | Unger et al. ............... | 424/450 |
| 5,849,727 A | 12/1998 | Porter et al. | |
| 5,961,459 A | 10/1999 | Kaul et al. | |
| 6,048,903 A * | 4/2000 | Toppo ......................... | 514/733 |
| 6,066,123 A | 5/2000 | Li et al. | |
| 6,068,857 A | 5/2000 | Weitschies et al. | |
| 6,071,495 A | 6/2000 | Unger et al. | |
| 6,117,858 A | 9/2000 | Porter et al. | |
| 6,120,751 A | 9/2000 | Unger | |
| RE36,939 E | 10/2000 | Tachibana et al. | |
| 6,135,976 A | 10/2000 | Tachibana et al. | |
| 6,139,819 A | 10/2000 | Unger et al. | |
| 6,265,387 B1 | 7/2001 | Wolff et al. | |
| 6,503,498 B1 * | 1/2003 | Gerard et al. .............. | 424/93.2 |
| 6,575,956 B1 | 6/2003 | Brisken et al. | |
| 2001/0008758 A1 | 7/2001 | McHale et al. | |
| 2001/0009904 A1 * | 7/2001 | Wolff et al. ................ | 514/44 |
| 2002/0165191 A1 | 11/2002 | Moonen et al. | |

FOREIGN PATENT DOCUMENTS

| | | |
|---|---|---|
| CN | 1056124 | 11/1995 |
| WO | WO 89/02464 | 3/1989 |
| WO | WO 00/42988 | 7/2000 |

OTHER PUBLICATIONS

Skyba et al. Circulation 1998:98:290-293.*
A. L. Klibanov, "Targeted delivery of gas-filled microspheres, contrast agents for ultrasound imaging", Advanced Drug Delivery Reviews 1999, vol. 37, pp. 139-157.
Author Unknown, "Microbubbles used to 'pop' new gene into the heart", Clinical Genetics, Oct. 11, 2000, vol. 58, No. 4, p. 269.
Manome, Yoshinobu, et al. "Ultrasound facilities transduction of naked plasmid DNA into colon carcinoma cells in vitro and in vivo" Blosis, Jul. 20, 2000.
Miller, D.L., et al. "Ultrasonic enhancement of gene transfection in murine melanoma tumors" Ultrasound in Medicine and Biology, New York, US, vol. 25, No. 9, Nov. 1999, pp. 1425-1430.
Kim, Hee Joong, et al. "Ultrasound-Mediated Transfection of Mammalian Cells" Human Gene Therapy, vol. 7, Jul. 10, 1996, pp. 1339-1346.
Lawrie, Allan, et al. "Ultrasound-Enhanced Transgene Expression in Vascular Cells is not Dependent Upon Cavitation-Induced Free Radicals" Ultrasound in Medicine And Biology, New York, US, vol. 29, No. 10, Oct. 2003, pp. 1453-1461.
Lawrie, A, et al. "Microbubble-enhanced ultrasound for vascular gene delivry" Gene Therapy, vol. 7, Dec. 2000, pp. 2023-2027.
Manome, Y. et al. "Ultrasound Facilitates Transduction of Naked Plasmid DNA into Colon Carcinoma Cells in Vitro and in Vivo." Human Gene Therapy, 2000; 11:1521-1528.
Anwer, K. et al. "Ultrasound enhancement of cationic lipid mediated gene transfer to primary tumors following systemic administration" Gene Therapy, 2000; 7:1833-1839.
Tangirala, R.K. et al. "Regression of atherosclerosis induced by liver-directed gene transfer of apolipoprotein A-I in mice" Circulation. 1999;100(17):1816-22.
Dansky, H.M. et al. "High-Density Lipoprotein and Plaque Regression" Editorial in: Circulation. 1999; 100(17):1762-1763.
Tsukamoto, K. et al. "Comparison of human apoA-I expression in mouse models of atherosclerosis . . . " J Lipid Res. 1997; 38(9):1869-76.
Boisvert, W.A. et al. "ApoA1 reduces free cholesterol accumulation in atherosclerotic lesions . . . " Arterioscler Thromb Vasc Biol. 1999;19(3):525-30.
Huber, P.E. et al. "In vitro and in vivo transfection of plasmid DNA in the Dunning prostate tumor R3327-AT1 . . . " Gene Therapy, 2000; 7:1516-1525.

(Continued)

Primary Examiner—Brian Whiteman

(57) ABSTRACT

A method for transfection of DNA or RNA encoding apo A1 into the liver to regulate lipid metabolism comprises injection of a solution containing the DNA or RNA gene into the liver in combination with gas microbubbles or microspheres and using ultrasound to induce the transfection of the DNA or RNA in the liver.

14 Claims, No Drawings

OTHER PUBLICATIONS

Shohet, R.V. et al., "Echocardiographic destruction of albumin microbubbles directs gene delivery to the myocardium" Circulation, 2000;101(22):2554-2556.

Lawrie, A. et al., "Ultrasound enhances reporter gene expression after transfection of vascular cells in vitro" Circulation, 1999; 99:2617-2620.

Dass, C. et al. "Apolipoprotein A-I, phospholipid vesicles, and cyclodextrins as potential anti-atherosclerotic drugs . . . " Drug Delivery, 2000; 7:161-182.

Nanjee, M.N. et al. "Acute effects of intravenous infusion of ApoA1/phosphatidylcholine discs", Arlerioscler Thromb Vasc Biol. 1999;19(4):979-89.

Chomas, J. et al. "Threshold of fragmentation for ultrasonic contrast agents" J. Biomed. Optics, 2001; 6(2):141-150.

Fechheimer, m. "Transfection of mammalian cells with plasmid DNA by scrape laoding and sonication loading" Proc. Natl. Acad. Sci. USA, 1987; 84:8463-8467.

Product insert for Optison ultrasound contrast agent, "Optison (Perflutren Protein-Type A Microspheres for Injection, USP", revised Jun. 2003.

* cited by examiner

ENHANCEMENT OF TRANSFECTION OF DNA INTO THE LIVER

CROSS-REFERENCE TO RELATED APPLICATIONS

This application is the National Stage of PCT/US02/21620, filed on Jul. 10, 2002, which claims the benefit of U.S. Provisional Application Ser. No. 60/303,784, which was filed on Jul. 10, 2001.

FIELD OF THE INVENTION

The invention relates to the transfection of DNA into the liver of a mammal, and more particularly relates to the ultrasonic microsphere enhancement of the transfection of DNA into the organs of a mammal, particularly the liver.

BACKGROUND OF THE INVENTION

One approach to improve the efficacy of in vivo gene therapy, with the aim at enhancing expression of a transgene, involves utilization of ultrasound to facilitate transfection of DNA into cells. Manome et al., *Circulation*, 99(20):2617–20 (1999), incorporated herein by reference, disclose transfection of naked plasmid DNA into colon carcinoma cells in vitro and in vivo by using ultrasound. In this study, a reporter pcDNA3-lacZ plasmid, containing *Escherichia coli* lacZ or the beta-galactosidase gene (beta-gal), and a neomycin 3'-phosphotransferase gene (neo) has been used for evaluation of transfer efficiency. MC38 cells, murine colon carcinoma cells, have been implanted in syngeneic mice and plasmid with naked DNA injected in the mice and the cells. The cells were subjected to continuous ultrasound exposure at 1.0-MHz, 20 W/cm$^2$. In a transient assay, significant numbers of cells were transduced with the beta-galactosidase gene.

Lawrie et al., *Circulation*, 99(20):2617–20(1999), reported that ultrasound enhances gene expression after transfection of vascular cells in vitro. Lawrie et al. investigated the use of adjunctive ultrasound to enhance nonviral gene delivery. In this study, cultured porcine vascular smooth muscle cells and endothelial cells were transfected with naked or liposome-complexed luciferase reporter plasmid. The luciferase activity after lipofection of endothelial cells was enhanced by adjunctive ultrasound exposure. Ultrasound exposure had no effect on cell viability, although it inhibited vascular smooth muscle cells, but not endothelial cell proliferation.

Shohet et al., *Circulation*, 101(22):2554–6(2000), incorporated herein by reference, describe a noninvasive method for transduction of a gene. In this study, recombinant adenovirus containing beta-gaactosidase and driven by a constitutive promoter was attached to the surface of albumin-coated, perfluoropropane-filled microbubbles. Then, microbubbles were infused into the jugular vein of rats with or without simultaneous echocardiography to effectively deliver the adenovirus to rat myocardium. The hearts of all rats that underwent ultrasound-mediated destruction of microbubbles containing virus showed myocardial expression of the beta-galactosidase transgene.

Huber et al, *Gene Ther.* 7(17):1516–25(2000), reported that gene therapy, as a form of molecular medicine, is expected to have a major impact on medical treatments in the future, but that the clinical use of gene therapy is hampered by inadequate gene delivering systems to ensure sufficient, accurate and safe DNA uptake in the target cells in vivo. Huber et al. reported that nonviral transfection methods might have the advantage of safe application, but it would be helpful to increase their transfection rates, especially in vivo. Huber's studies focused on using ultrasound to provide an enhanced transfer of DNA plasmids in vitro and in vivo. In vitro, the beta-galactosidase and luciferase DNA reporter plasmid were transfected into four cell lines (NIH 3T3 fibroblasts, malignant melanoma Mewo, HeLa, Dunning prostate tumor R3327-AT1). Ultrasound induced a 55-(Mewo) to 220-fold (AT1) stimulation resulting in transfection efficiencies in vitro between 2% (Mewo) and 12% (AT1). The in vivo stimulation was assessed in the Dunning prostate tumor R3327-AT1 implanted subcutaneously in Copenhagen rats using the beta-galactosidase reporter. After intratumoral DNA injection, focused ultrasound induced a 10-fold increase of beta-galactosidase positive cells in histology and a 15-fold increase of beta-galactosidase protein expression in the ELISA assay. In contrast, ultrasound was not found to enhance reporter gene expression after intravenous plasmid application.

In another study, Anwer et al., *Gene Ther.* 7(21):1833–9 (2000), investigated the impact of a localized application of ultrasound on gene transfer to primary tumors following systemic administration of cationic lipid based transfection complexes. Anwer et al. reported that it had been previously shown that systemic administration of (N-[(1-(2-3-dioleyloxy)propyl)]-N—N—N-trimethylammonium chloride): cholesterol-based transfection complexes to tumor-bearing mice resulted in expression in the tumor and other tissues, primarily the lungs.

A microbubble-enhanced ultrasound technique for vascular gene delivery was reported by Lawrie et al., *Gene Ther.;* 7(23):2023–2027 (2000), incorporated herein by reference. Lawrie noted that progress in cardiovascular gene therapy has been hampered by concerns over the safety and practicality of viral vectors and the inefficiency of current nonviral transfection techniques.

U.S. Pat. Re. 36,939 to Tachibana et al. describes a booster comprising microbubbles of a gas in a liquid, e.g. about 4×10$^7$ cells/ml of microbubbles of a gas having a diameter of 0.1 to 100 um in 3 to 5% human serum albumin solution, and a pharmaceutical liquid composition comprising the booster and a medicament, which are useful for the therapy of various diseases together with exposure to ultrasonic waves.

U.S. Pat. No. 5,542,935 to Unger, et al., discloses a therapeutic delivery system comprising gaseous precursor-filled liposomes having encapsulated therein a contrast agent or drug.

PCT publication W08902464 discloses a method of introducing material into living mammalian cells, or of fusing material with the cells. The method comprises subjecting the cells in liquid suspension in the presence of the material to ultrasonic excitation sufficient to traumatize the cells. The material introduced into the cells, or into a cell membrane, is preferably DNA or RNA or a protein.

China Patent No. 1056124 discloses a gene conduction method using ultrasonic waves for genetic engineering of both animals and plants. A biological material in DNA solution treated with an ultrasonic wave causes the cell membranes of the biological material to change in structure such that DNA molecules in the solution may diffuse into the cells.

PCT publication W09806864 discloses methods for using local heat to control gene expression. The heat shock protein (hsp) gene promoter is recombined with a selected therapeutic gene and expressed in selected cells. Local controlled heating is used to activate the hsp promoter, for example by using focused ultrasound.

PCT publication W00042988 discloses a method of identifying and/or treating tissue having leukocytes adhered thereto which utilizes a material that selectively attaches to leukocytes adhered to a patient's tissue. The material may be a gas-filled microbubble contrast agent that selectively attaches to activated inflamed tissue. The microbubbles attached to activated leukocytes may be located by ultrasound echography, and inflamed tissue may be treated by a drug or gene sequence carried by the microbubble contrast agent.

U.S. Pat. No. 6,265,387 BI and PCT application WO 00/50617, published Aug. 31, 2000 disclose methods for gene therapy which involve the delivery of a polynucleotide to a cell in a mammal by injecting the polynucleotide into a blood vessel connected to the cell such that the polynucleotide is transfected into the cell and expressed to therapeutic levels. In these disclosures, this intravascular route of administration is increased by increasing the permeability of the tissues blood vessel by increasing the intravascular hydrostatic (physical) pressure or increasing the osmotic pressure.

According to the present invention, gene expression in the liver is accomplished by injecting DNA or equivalent into the blood peripherally and isonifying the liver with ultrasound. The ultrasound waves alone, when enhanced by disrupted microspheres, optionally with increased injection pressure, will result in efficient transfection of DNA or equivalent into the nucleus.

SUMMARY OF THE INVENTION

It is accordingly an object of this invention is to provide a method for inducing gene expression in cells such as those of the liver or other organ of a mammal.

A further object of the invention is to provide a method for the transfection of DNA or equivalent into the liver.

An even further object of the invention is to provide a new and improved method for the transfection of a desired DNA or equivalent into the liver using a technique involving microspheres and ultrasound, and optionally increased injection pressure.

It is a still further object of the invention to induce apo A1 gene expression by injecting apo A1 genetic material into the liver and enhancing expression of the apo A1 gene using ultrasound and microspheres to facilitate transfection of the apo A1 gene in the liver cells.

The above and other objects, features and advantages of this invention will become apparent upon reading the following detailed description and referring to the accompanying drawing.

In satisfaction of the foregoing objects and advantages, the present invention provides a new and novel gene therapy method for the transfection of a DNA or equivalent into the liver or other organ of a mammal, the method comprising the steps of:

a) delivering the DNA or equivalent to the vasculature of the liver; and b) applying ultrasound to the liver during liver exposure to the DNA to induce the expression of the DNA in the liver.

In further embodiments, microspheres or microbubbles are injected into the blood to enhance the transfection process. In a further optional embodiment, increased injection pressure of the DNA or equivalent is applied to enhance the transfection procedure.

DESCRIPTION OF THE INVENTION

The present invention comprises materials and methods for the transfection of polynucleotides such as DNA and RNA into an organ of a mammal such as the liver. The method utilizes intravascular administration of a DNA containing solution using high injection pressure, ultrasound treatment of the target organ such as the liver, or combinations of ultrasound treatment and injection pressure and/or combinations thereof with microbubbles or microspheres, or any combination of these procedures.

In this invention, DNA or equivalent means DNA, any plasmid DNA or other forms of DNA that may be actively translated once incorporated into a mammalian cell. The DNA is preferably used in a solution which may be formulated with an ultrasound active agent, such as small gas bubbles. The gas bubbles may be in the form of encapsulated gas microspheres or gas bubbles stabilized by materials such as surfactants, lipids, proteins, lipoproteins, and polymers. The gas may be comprised of any species of gas, but physiologically compatible gases such as air and nitrogen are preferred. The gas bubbles are preferably near the size of red blood cell or less, approximately 7 microns in diameter, to allow free circulation of the bubbles in the blood system.

The term "transfection" as used herein, in general, means delivery, or, more specifically, the transfer of a polynucleotide from directly outside a cell membrane to within the cell membrane. If the polynucleotide is a primary RNA transcript that is processed into messenger RNA, a ribosome translates the messenger RNA to produce a protein within the cytoplasm. If the polynucleotide is a DNA, it enters the nucleus where it is transcribed into a messenger RNA that is transported into the cytoplasm where it is translated into protein. The polynucleotide contains sequences that are required for its transcription and translation. These include promoter and enhancer sequences that are required for initiation. DNA and thus the corresponding messenger RNA (transcribed from the DNA) contain introns that must be spliced, poly A addition sequences, and sequences required for the initiation and termination of its translation into protein. Therefore if a polynucleotide expresses its cognate protein, then it must have entered a cell.

A polynucleotide such as DNA or RNA can be delivered to a cell in order to produce a cellular change that is therapeutic. The delivery of polynucleotides or other genetic material for therapeutic purposes is described as gene therapy. The polynucleotides are coded to express a whole or partial protein, and can be delivered either directly to the organism in situ or indirectly by transfer to a cell that is then transplanted into the organism. The DNA or RNA can be the nucleotide of any therapeutic reagent useful in gene therapy such a serum Apo A1 or luceriferase enzyme.

In a liver organ, the parenchymal cells include hepatocytes, Kupffer cells and the epithelial cells that line the biliary tract and bile ductules. The major constituent of the liver parenchyma are polyhedral hepatocytes (also known as hepatic cells) that presents at least one side to an hepatic sinusoid and opposed sides to a bile canaliculus. Liver cells that are not parenchymal cells include cells within the blood vessels such as the endothelial cells or fibroblast cells.

In the present invention, a polynucleotide is delivered into a liver blood vessel at distal or proximal points. A liver blood vessel includes the portal venous system which transports blood from the gastrointestinal tract and other internal organs (e.g. spleen, pancreas and gall bladder) to the liver. Another liver blood vessel is the hepatic vein. The hepatic vein may also be reached via the inferior vena cava or another blood vessel that ultimately connects to the liver. A needle or catheter is used to inject the polynucleotide into the vascular system. The injection can be performed under direct observation following an incision and visualization of the tissues blood vessels. Alternatively, a catheter can be inserted at a distant site and threaded so that it resides in the vascular system that connects with the target tissue. In another embodiment, the injection can be performed by using a needle that traverses the intact skin and enters a vessel that supplies or drains from the target tissue.

In the liver, the hepatic vein is an efferent blood vessel since it normally carries blood away from the liver into the inferior vena cave. Also in the liver, the portal vein and hepatic arteries are afferent blood vessels in relation to the liver since they normally carry blood towards the liver. Plasmid DNA may be efficiently expressed if delivered into the effluent vessel of the liver (i.e. the hepatic vein).

In the method of the invention a polynucleotide such as DNA and/or RNA is transfected into the liver using ultrasound techniques optionally combined with injection pressure.

In conducting the method, the DNA or RNA is formed into a solution with a transfection reagent and then injected vascularly. The DNA or RNA solution is preferably formulated with an ultrasound active agent such as small gas bubbles, the bubbles being small enough in diameter to permit circulation in the blood system. The microbubbles are formed by entrapping microspheres of a gas into a liquid. The gas may be any desired gas but for safety reasons should be a physiological gas such as air, oxygen or nitrogen, or alternatively an inert gas such as noble gases, sulfur hexafluoride or perfluorocarbon gases. The liquid is preferably a physiological saline solution (about 1 to 8 wt. %), an aqueous glucose solution, a solution of human serum albumin solution or the like with physiologically compatible pH and osmolarity. Preferably the bubbles are about 0.01 to about 7 microns in diameter.

In a further embodiment, the injection pressure may be increased by any known method such as occlusions or as a function of the injector device. The injection pressure is preferably that pressure achieved by administration of about 1 to 500 ml of solution in about 2 to 10 seconds. The pressure however should be below that which might damage the liver. A suitably equipped infusion pump may be used to increase the injection pressure.

For the ultrasound treatment, an ultrasound contrast agent is included in the DNA or RNA solution. Such contrast agents are commercially available and include OPTISON® ultrasound contrast agent from Molecular Biosystems in San Diego, Calif., as well as aqueous indocyanine green solution, agitated hypertonic saline, autoblood, or aqueous maglumine diatriazoate, or the like.

The ultrasound may be applied by known ultrasonic devices which preferably provide an ultrasonic signal of 0.5 to 10.0 MHz.

The method of the invention may be used alone or in combination with other forms of therapy including in conjunction with a chemotherapeutic agent such as in the treatment of tumors.

The apo-A1 gene produces apolipoprotein A1, which plays an active role in reducing atherosclerosis that is associated with coronary heart disease. HDL-cholesterol (HDL) is inversely correlated with the development of coronary heart disease. High levels of HDL reduce the risk of coronary heart disease, and low levels are associated with a marked increase risk of premature coronary heart disease.

HDL reduces the risk of coronary heart disease presumably, in most part, by promoting the efflux of cholesterol from peripheral cells (especially arterial macrophages) and transports the cholesterol to the liver for catabolism. This process is known as reverse cholesterol transport.

The reverse cholesterol transport progress begins with the interaction of a nascent HDL particle that contains apolipoprotein A1 and is devoid of substantial lipid contents with the ABC1 transporter protein on cell surfaces. The ABC1 transporter protein interacts with the nascent HDL to promote the efflux of cholesterol into the HDL particle. Apolipoprotein A1 activates a plasma enzyme lecithin, cholesterol acyltransferase (LCAT), that esterifies the free cholesterol to cholesterol ester. The hydrophobic nature of cholesterol ester moves it into the core of HDL and the flat, nascent HDL particle becomes spherical in shape coated with cholesterol ester. This mature HDL particle unloads its cholesterol ester by transferring the lipids to VLDL (very low density lipoprotein) cholesterol ester transfer protein (CETP) or the cholesterol ester is taken up by the liver utilizing the scavenger receptor B1 (SRB1) receptor.

The Apolipoprotein A1 is synthesized in the liver and the intestines. Its amino acid sequence has been identified. To date, however, there is little information available to determine how apo A1 is synthesized and, therefore, drugs that upregulate apo A1 synthesis have not yet been developed.

Apo A1 knockout mice show increased development of atherosclerosis. Gene therapy utilizing a viral vector has increased apolipoprotein A1 levels in these knockout mice and reduced atherosclerosis. Since the liver is the main organ involved in the synthesis of apolipoprotein A1, repeated viral vector inoculation to induce apo A1 gene transduction in humans, at present, is potentially harmful and is not a viable therapy in humans due to these safety concerns. Therefore, there is a need for safer and non-invasive routes to induce apo A1 gene expression in the liver.

This invention is especially suitable as a method for a non-invasive route to induce genes such as the apo A1 gene expression in the liver. In this procedure, a naked plasmid apo A1 DNA is injected into the blood peripherally via a microsphere or microbubble containing formulation using the above-described methods optionally using increased injection pressure. The capillary endothelial cells in the liver are fenestrated, thus, may permit enhanced uptake of plasmids into the liver cells. The liver cells are then treated with ultrasound waves that disrupt the microspheres and cause transient porosity of the endothelial liver cells, allowing for the entrance of the apo A1 DNA and transfection of the DNA into the nucleus of the endothelial cells.

In a specific method, albino mice (CD-1 weighing approximately between 20 and 30 grams), have 200 mg of naked plasmid beta-galactosidase DNA (a reporter gene) injected into the tail vein of 3–6 mice with a microbubble such as OPTISON® ultrasound contrast agent, which is a suspension of microspheres comprising a perfluorocarbon gas encapsulated within human serum albumin, while the liver is sonicated with a standard ultrasound imaging device. After 3 days, the mice are sacrificed and the liver tissue recalculated for percent of cells with the transduced beta-galactosidase gene.

The mice experiments evaluate the optimal dose of the DNA, the microbubble, and the length and exact location of the insonification with ultrasound. The plasmids may be located inside the spheres, on the inner shell, throughout the shell, or on the surface. Other alternatives include utilizing liposomal DNA or combining the reporter DNA with VEGF, which may enhance transfection rates into the blood peripherally with microspheres containing the apo A1 plasmid and insonifying the liver with ultrasound. The ultrasound waves alone, and enhanced by the disrupted microsphere, will result in transient porosity of the endothelial liver cells, allowing for the entrance of the Apo A1 DNA and transfection of the DNA into the nucleus.

Once the dose of microspheres and DNA are determined, Apo A1 knockout mice are infused with the combination of microspheres with naked Apo A1 plasmid DNA (other microspheres or other forms of DNA may be utilized) while the liver is insonified. The main efficacy endpoint will be levels of Apo A1 in the mouse plasma.

Obviously, many modifications and variations of the present invention are possible in light of the above teachings. It is therefore to be understood that, within the scope of the appended claims, the invention may be practiced otherwise than as specifically described herein.

EXAMPLE 1

Transfection of the Liver of a Mouse with Combinations of Ultrasound and High Pressure Four groups of mice were treated with an injection of a DNA plasmid coding for luceriferase enzyme (I. Danko, et al., Gene Therapy 1, 114, 1994), directed toward the liver. Mice weighing 20–23 grams were anesthetized with Isoflurane. A midline abdominal incision was made and the portal vein was cannulated with a 27-gauge butterfly needle. Using a Harvard infusion pump, a formulation containing plasmid DNA was administered to the animal. After 24 hours, the livers of the animals were collected and assayed for luciferase activity. Small sections of liver were also prepared for pathology evaluation. Blood was collected to assay for ALT (alanine aminotransferase) as an indicator of liver damage.

Group 1: High Pressure Delivery

Three mice were given a 1.0 ml of saline, containing 50 micrograms of DNA, injected over a 10 second time period. The IVC both below and above the liver was occluded for 2 minutes duration while the injection was performed to create high pressure within the liver during the injection.

Group 2: Ultrasound Delivery

In the first mouse, the IVC below the liver was occluded prior to injection of DNA, consisting of 50 micrograms of DNA in 0.2 ml of TRANSIT® transfection reagent (Mirus Corporation, Madison Wis.), mixed with 0.3 ml of OPTISON® ultrasound contrast agent (Molecular Biosystems, San Diego, Calif.). The second and third mouse received no IVC occlusion and 0.2 ml of saline containing 50 micrograms of DNA mixed with 0.3 ml of OPTISON® ultrasound contrast agent.

All DNA solutions were continuously infused over a 1 minute period of time and ultrasound imaging of the liver was performed for 1 minute using a General Electric ultrasound imaging system (Model VIVID5). The tip of the transducer was placed into the thumb of a rubber glove filled with Aqua-gel. On the tip of the rubber glove a small amount of contact gel was used when placed over the liver. The ultrasound settings were as follows: mechanical index at 0.5, frame rate set at 52 frames/sec., imaging depth set at 5 cm and frequency of 1.6 MHz. On every injection the ultrasound contrast agent was observed by the ultrasound imaging system within the liver.

Group 3: Combined Ultrasound and High Pressure Delivery

Three mice were prepared and treated similarly to Groups 1 and 2. The mice received a total volume of 1 ml (50 micrograms of naked DNA in 0.4 ml saline with 0.6 ml OPTISON® ultrasound contrast agent) over 10 seconds while maintaining IVC occlusions above and below the injection site for 2 minutes. The liver was imaged for one minute similar to treatment of Group 2.

Results:

|  | Relative Luciferase Units | Liver Pathology | ALT (liver function test) |
|---|---|---|---|
| Group 1 - High Pressure (n = 3) | 17,316,343 average | Few small spots Blotchy, hard areas Normal | 150 767 365 |
| Group 2 - Ultrasound (n = 3) | 42,578 average | Normal Normal Normal | 45 111 138 |
| Group 3 - High Pressure and Ultrasound (n = 2) | 52,181,055 average | Blotchy, hard areas Blotch, hard areas | 930 2149 |
|  | 225 Luciferase Assay Background |  | 32 Naïve mouse |

Ultrasound treatment of the liver during administration of the DNA containing formulation was able to transfect the DNA plasmid to the liver at a mean level 189 times greater than baseline. High pressure and the combination of high pressure with ultrasound were able to transfect even greater levels of luciferase DNA, but both appeared to cause an observable level of acute liver damage.

EXAMPLE 2

Transfection of the Liver of a Mouse with DNA Coding for Apo A1

Experiments were conducted applying ultrasound while injecting plasmid DNA into mice, similar to Example 1. The plasmid DNA was prepared to code for human apo A1 using a CMV promoter. Serum levels of apo A1 were measured from the treated animals at one, three, and seven days post treatment.

Group 1: High Pressure with Ultrasound

Each mouse was anesthetized with Isoflurane. A total volume of 1.5 ml of injectate composed of 250 micrograms of DNA in 187 microliters, 900 microliters of OPTISON® ultrasound contrast agent, and 412.5 microliters of saline, was delivered to the portal vein over a ten second period. Clamps were placed on the IVC above and below the liver prior to injection and removed two minutes after injection. Ultrasound was applied over the liver just prior to injection of the DNA and continued for one minute. The ultrasound was applied using a 2.5 MHz transducer operating at 1.5 MHz, with a depth of 2 cm, focal zone of 1 cm, mechanical index of 0.5, 52 frames/sec, and power setting of 8. The ultrasound was applied as described in experiment 1, using a gel filled latex glove to form a two-centimeter standoff for the transducer.

Group 2: High Pressure Tail Vein Injection

Each mouse was injected with 1.9 ml of injectate, comprising 10 micrograms of DNA in 1.9 ml of Ringers solution.

The injectate was delivered over a 2 to 3 second period.

Group 3: High Pressure Tail Vein Injection with Ultrasound

Each mouse was injected with 1.9 ml of injectate as described for Group 2, except that the injectate also comprised 950 microliters of OPTISON® ultrasound contrast agent and was delivered over a 4 to 5 second period. The liver was treated with ultrasound as described for Example 1 except that the ultrasound was applied for 30 seconds from the start of delivery of the injectate. The ultrasound was primarily directed to the right lobe of the liver.

Results:

| | Serum apo A1 mg/dl | | | |
|---|---|---|---|---|
| | Day 1 | Day 3 | Day 7 | Notes |
| Group 1 - High Pressure with Ultrasound (n = 6) | 25.7 | 20.0 | 17.3 | Blotchiness of left lobe of liver on mouse #6, blanching of left lobe on mouse #2. |
| Group 2 - High Pressure Tail Vein Injection (n = 7) | 68.0 | 23.5 | 15.5 | Injected over 2–3 seconds to create high pressure. |
| Group 3 - Medium Pressure Tail Vein Injection with Ultrasound (n = 2) | 39.5 | 19.5 | 17.5 | Injected over 4–5 seconds to reduce pressure. |
| Controls (no treatment) (n = 2) | 14.0 | 13.0 | 15.0 | |

Administration of the apo A1 DNA containing formulation to the liver was able to transfect the DNA plasmid to a mean level greater than baseline when delivered under high pressure or a combination of pressure and ultrasound. Acute liver damage was observed from some animals treated with a combination of high pressure and ultrasound.

The invention has been described with reference to certain preferred embodiments, however, as obvious variations thereon will become obvious to those of skill in the art, the invention is not considered to be limited thereto.

What is claimed Is:

1. A method for in vivo transfection of DNA encoding apo A1 into liver cells of a mammal comprising the steps of
   a) delivering a solution containing (i) an ultrasonic contrast agent comprising protein-stabilized gas microspheres, and (ii) plasmid DNA which encodes apo A1 to the vasculature of the liver under pressure; and
   b) applying ultrasound to the liver during exposure of the liver cells to the solution to induce the transfection of the DNA in the liver cells to increase the level of apo A1 in the blood of the mammal.

2. The method according to claim 1, wherein the gas is air, nitrogen, or oxygen.

3. The method according to claim 1, wherein the solution is delivered to the liver by injecting the solution into the blood peripherally.

4. The method according to claim 1, wherein the transfected DNA alters cholesterol metabolism of the liver.

5. The method according to claim 1, wherein the DNA encodes apo A1, operably linked to a promoter.

6. The method of claim 1, wherein the ultrasound is applied locally to the liver.

7. A method for the in vivo transfection of the apo A1 gene in liver cells to regulate cholesterol comprising the steps of:
   a) forming protein-stabilized gas filled microspheres containing plasmid DNA comprising the apo A1 gene;
   b) delivering the microspheres into the vasculature of the liver under pressure, and
   c) applying ultrasound to the microspheres to induce the transfection of the apo A1 gene in the liver cells to increase the level of apo A1 in the blood.

8. The method according to claim 7, wherein the microspheres are injected into the blood peripherally.

9. The method of claim 1, wherein the gas is a fluorocarbon gas.

10. The method of claim 1, wherein the microspheres are encapsulated by human serum albumin.

11. A method for in vivo transfection of an apo A1 gene into liver cells of a mammal comprising the steps of:
    a) injecting into the vasculature of the liver an aqueous composition containing a plasmid DNA encoding apo A1 mixed with gas filled microspheres comprising a fluorocarbon gas encapsulated within human serum albumin; and
    b) applying ultrasound to the liver during injection of the composition to induce transfection of the plasmid DNA in the liver cells and increase the level of apo A1 in the blood of the mammal.

12. The method of claim 11, wherein the plasmid DNA is operably linked to a promoter.

13. The method of claim 11 wherein the ultrasound is applied to the liver with an ultrasonic imaging device and is utilized to image the liver while inducing transfection.

14. The method of claim 1 wherein the ultrasound is applied to the liver with an ultrasonic imaging device and is utilized to image the liver while inducing transfection.

* * * * *

UNITED STATES PATENT AND TRADEMARK OFFICE
CERTIFICATE OF CORRECTION

| | | |
|---|---|---|
| PATENT NO. | : 7,211,248 B2 | Page 1 of 1 |
| APPLICATION NO. | : 10/483189 | |
| DATED | : May 1, 2007 | |
| INVENTOR(S) | : Michael Davidson | |

It is certified that error appears in the above-identified patent and that said Letters Patent is hereby corrected as shown below:

SPECIFICATION - BACKGROUND OF THE INVENTION

Column 2, line 33, delete "Ther.;" and insert --Ther.,;--

Signed and Sealed this

Twenty-eighth Day of July, 2009

JOHN DOLL
*Acting Director of the United States Patent and Trademark Office*